United States Patent
Alotaibi et al.

(10) Patent No.: US 9,320,577 B1
(45) Date of Patent: Apr. 26, 2016

(54) JOINT ASSEMBLY FOR DENTAL IMPLANT ABUTMENT

(71) Applicant: KING SAUD UNIVERSITY, Riyadh (SA)

(72) Inventors: Hanan Nejer Sahil Alotaibi, Riyadh (SA); Sulieman Saleem B. Al-Johany, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 66 days.

(21) Appl. No.: 14/672,047

(22) Filed: Mar. 27, 2015

(51) Int. Cl.
*A61C 8/00* (2006.01)

(52) U.S. Cl.
CPC .............. *A61C 8/0053* (2013.01); *A61C 8/0074* (2013.01)

(58) Field of Classification Search
USPC ........................................ 433/172–176, 201.1
See application file for complete search history.

(56) References Cited

U.S. PATENT DOCUMENTS

| | | | |
|---|---|---|---|
| 4,832,601 A * | 5/1989 | Linden | 433/173 |
| 4,842,518 A * | 6/1989 | Linkow et al. | 433/174 |
| 4,907,969 A * | 3/1990 | Ward | 433/173 |
| 5,302,125 A | 4/1994 | Kownacki et al. | |
| 5,417,570 A | 5/1995 | Zuest et al. | |
| 5,516,288 A | 5/1996 | Sichler et al. | |
| 5,564,925 A * | 10/1996 | Shampanier | 433/173 |
| 6,030,219 A | 2/2000 | Zuest et al. | |
| 6,500,003 B2 | 12/2002 | Nichinonni | |
| 7,214,063 B2 | 5/2007 | Cohen | |
| 8,512,039 B2 | 8/2013 | Mullaly et al. | |
| 8,678,822 B2 | 3/2014 | Seo | |
| 2003/0224329 A1 * | 12/2003 | Carlton | 433/173 |
| 2004/0005530 A1 | 1/2004 | Mullaly et al. | |
| 2009/0246734 A1 * | 10/2009 | Bar Shalom | 433/173 |
| 2010/0184004 A1 * | 7/2010 | Fromovich | 433/174 |
| 2011/0287381 A1 * | 11/2011 | Sanders | 433/75 |
| 2014/0178838 A1 | 6/2014 | McBride et al. | |
| 2014/0302457 A1 * | 10/2014 | Siegmund | 433/173 |

FOREIGN PATENT DOCUMENTS

CH           696 625 A5     8/2007

* cited by examiner

*Primary Examiner* — Matthew Nelson
(74) *Attorney, Agent, or Firm* — Richard C. Litman

(57) ABSTRACT

The joint assembly for dental implant abutment includes an abutment section adapted for attachment to a dental implant and a ball section selectively mounted to the abutment section at a user-selectable angle. The abutment section includes a base member having a recessed socket. A plurality of threaded bores radiate into the base member from the socket. The ball section includes a spherical head having a threaded post extending therefrom for mounting the ball joint into a user-selectable threaded bore in the socket to properly orient an integral locator mounting cap retained on the spherical head for attachment of a denture to the joint assembly. The angular orientation of the threaded bores allows a restorative dentist to adjust the joint assembly for effective mounting of the denture or other dental appliance.

4 Claims, 6 Drawing Sheets

JOINT ASSEMBLY FOR DENTAL IMPLANT ABUTMENT

BACKGROUND OF THE INVENTION

1. Field of the Invention

The present invention relates to dental prosthetics, and particularly to a joint assembly for dental implant abutment that provides versatile alignment for mounting or supporting a dental prosthesis with minimal adjustments and enhanced retention of dental appliances.

2. Description of the Related Art

Many different prosthetic options can be used for patients who are missing some or all of their teeth. Depending on the number and condition of the remaining teeth, the treatment options can range from fixed appliances or prostheses attached to the remaining teeth or attached to endosseous dental implants, removable partial appliances that gain retention from the remaining teeth, or removable complete appliances that rest on the oral mucosa.

A wide variety of endosseous dental implants are available in the market today, all of which share common features. These typically include a body with external threads, which is pretreated for insertion inside the jawbones and to facilitate osseointegration. The body of the implant also contains internal threads, which allows for a second part, usually called a prosthetic component, to be secured in the body of the implant.

In case of removable complete appliances, the patient lacks teeth that can enhance retention of the appliance. Due to this condition, two endosseous dental implants are typically implanted in the mandible to enhance the retention of the appliance. Different attachment systems or anchors are available to mount the appliance. These anchors can be attached to the roots of non-vital teeth, or to endosseous dental implants, usually two in number, that are placed in the canine teeth area.

The Locator® ("Locator" is a registered trademark of Zest Anchors, Inc. of Escondido, Calif.) is a common attachment assembly or anchor used by many dentists. This anchor is based on U.S. Pat. No. 6,030,219, issued to Zuest et al. Feb. 29, 2000, which is hereby incorporated by reference in its entirety. This anchor includes a female part attached to a non-vital tooth or to an endosseous dental implant, and a male part that can be attached to a dental appliance, e.g., removable complete or partial dentures. While this anchor is effective in providing a fixture for mounting the appliance, the anchor requires that the anchor implants be aligned or arranged substantially parallel to the corresponding mounting sockets in the appliance. The implant alignment or parallelism should be established early during the stage of surgically placing the implants in the jawbones. However, this is not always feasible because it depends on the availability of bone in the selected implant insertion area. The dental surgeon might be forced to tilt an implant in a direction where most of the bone is available. This type of situation can increase instances of misalignment that can decrease the effectiveness of mounting the appliance.

Thus, a joint assembly for dental implant abutment solving the aforementioned problems is desired.

SUMMARY OF THE INVENTION

The joint assembly for dental implant abutment includes an abutment section adapted for attachment to a dental implant and a ball section selectively mounted to the abutment section at a user-selectable angle. The abutment section includes a base member having a recessed socket. A plurality of threaded bores radiate into the base member from the socket. The ball section includes a spherical head having a threaded post extending therefrom for mounting the ball joint into a user-selectable threaded bore in the socket to properly orient an integral locator mounting cap retained on the spherical head for attachment of a denture to the joint assembly. The angular orientation of the threaded bores allows a restorative dentist to adjust the joint assembly for effective mounting of the denture or other dental appliance.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
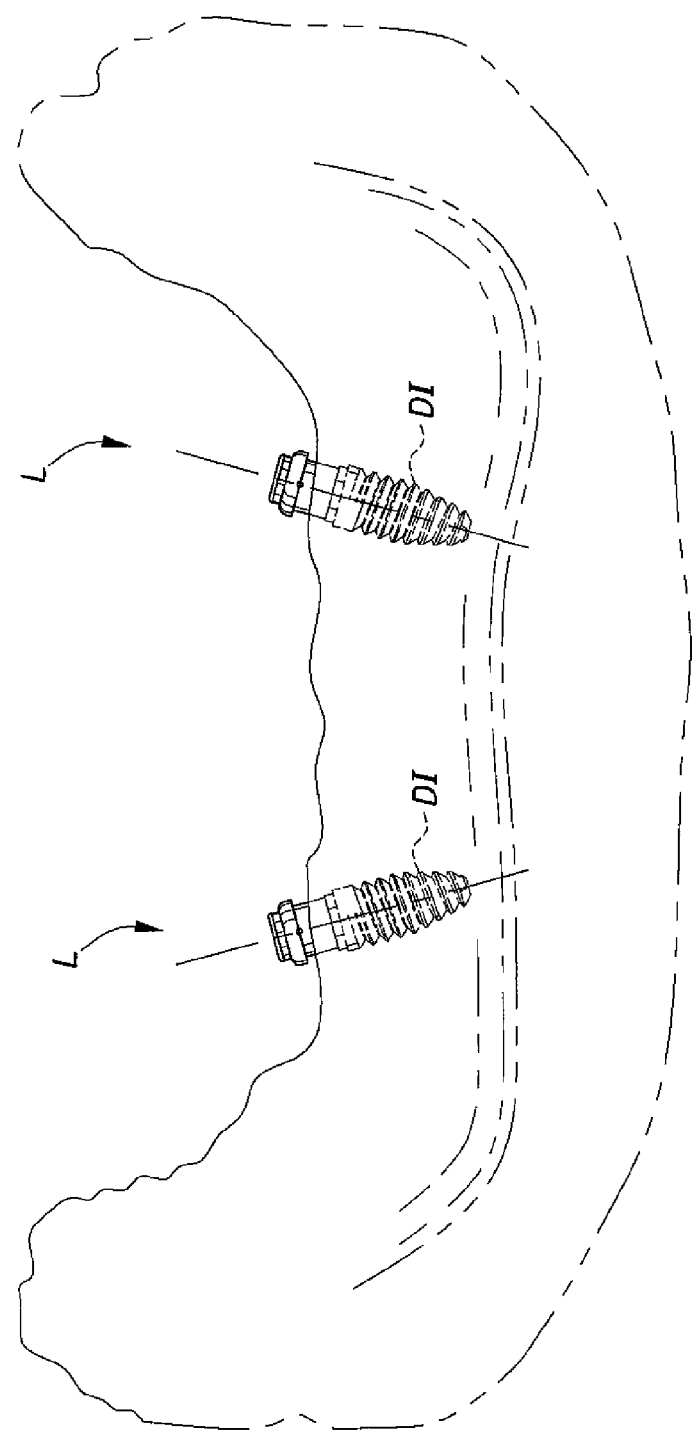
FIG. 1A is an environmental, perspective view of a prior art anchor arrangement.
Figure 1B:
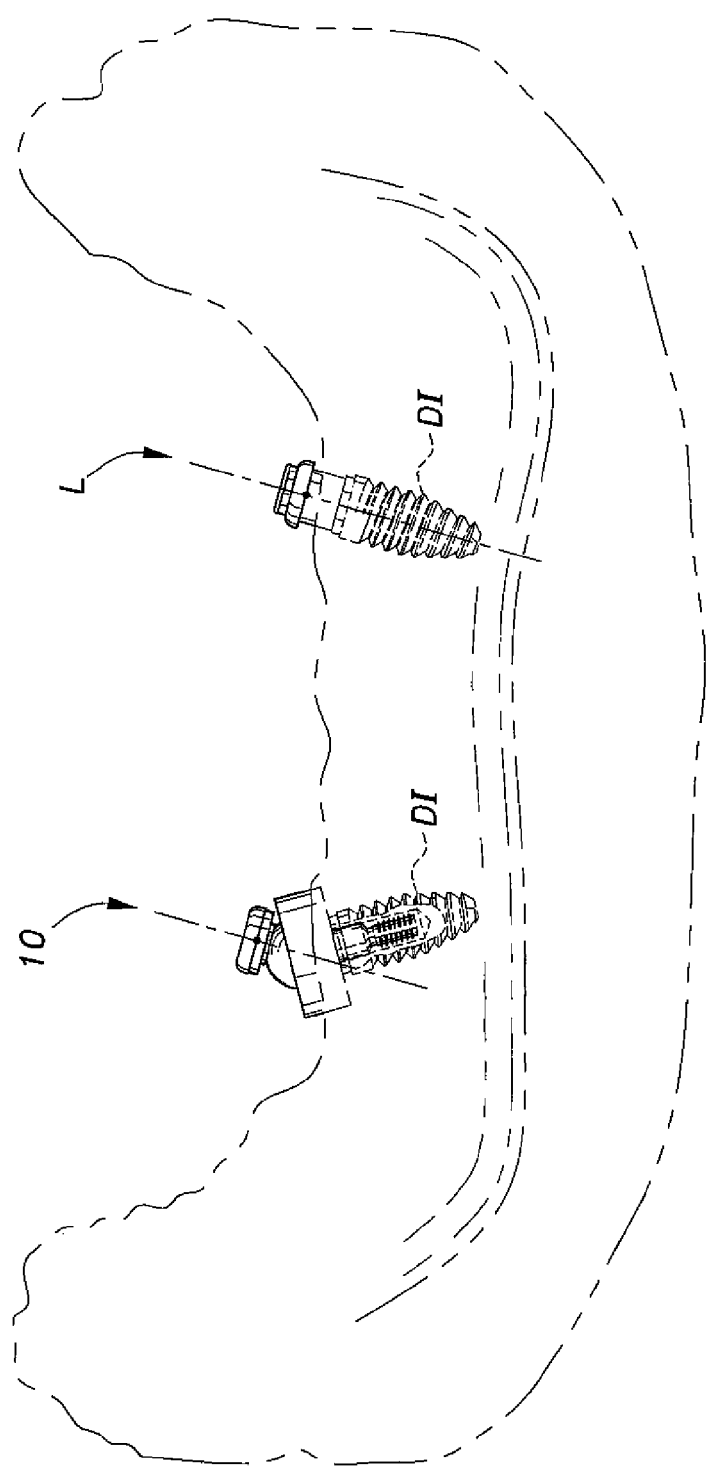
FIG. 1B is an environmental, perspective view of a joint assembly for dental implant abutment according to the present invention, as may be used in conjunction with a prior art anchor assembly.
Figure 2:
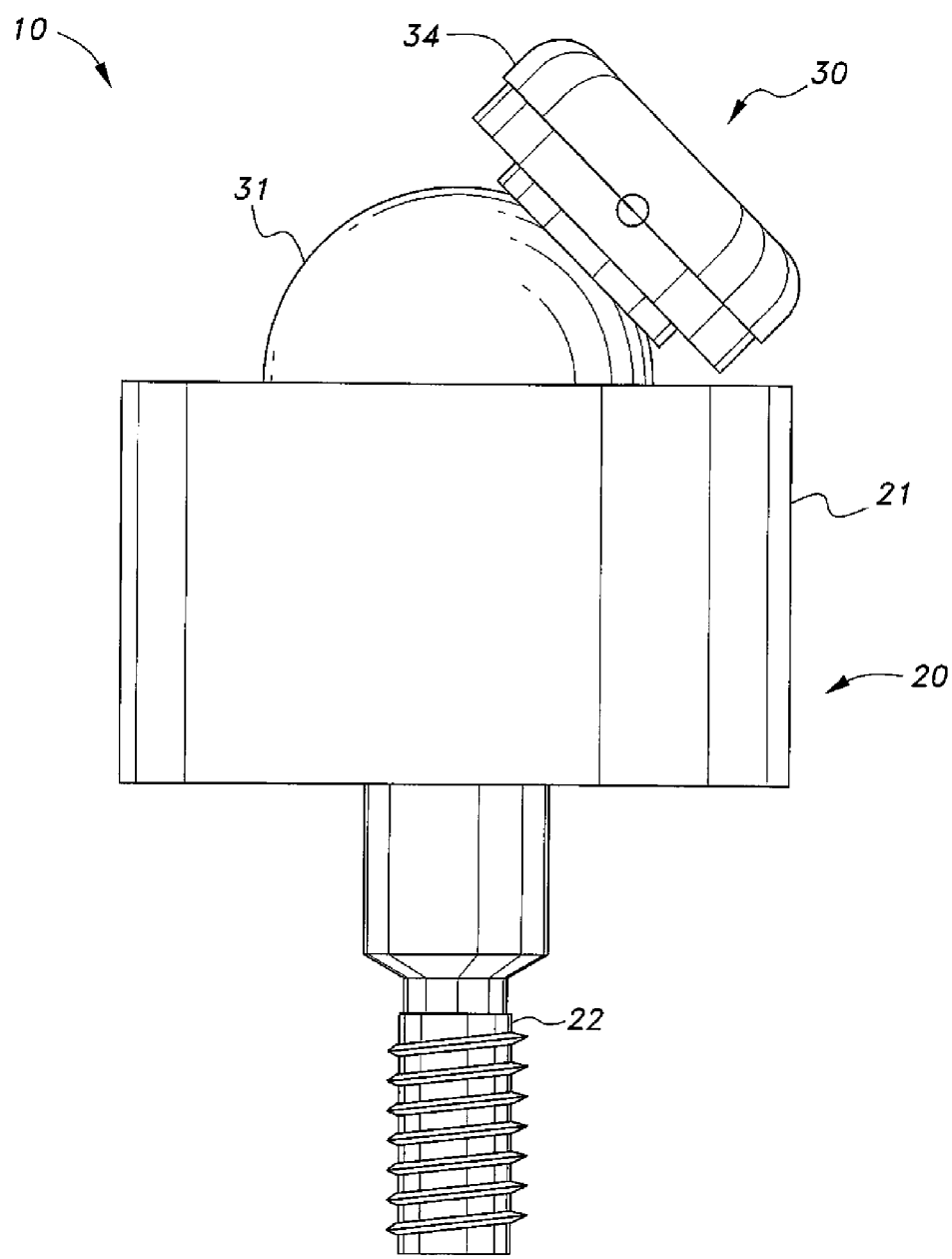
FIG. 2 is a front view of the joint assembly for dental implant abutment of FIG. 1.

The joint assembly for dental implant abutment, generally referred to by the reference number 10 in the drawings, provides an easily adjustable joint to facilitate proper alignment for a variety of dental prostheses. As shown in FIGS. 1A, 1B, and 2, the joint assembly 10 includes an abutment section 20 adapted for attachment to an implant DI and a ball section 30 selectively attached to the abutment section 20.

The abutment section 20 includes a base member 21 and a substantially elongate threaded post 22 extending from the bottom surface of the base member 21. As best seen in FIG. 1B, the threaded post 22 is configured to be threaded into an internally threaded bore in the implant DI, which has been surgically implanted into the patient's mandible at a preselected area. As shown, one joint assembly 10 is installed along an edentulous patient's mandible spaced from a prior art anchor L. In comparison with FIG. 1A, a pair of installed, prior art anchors L is shown to be extending at divergent angles due to the patient's specific mandible structure and available bone. The divergent angular orientation of the anchors L renders subsequent mounting of a dental appliance very difficult. In contrast, the ball section 30 of the joint assembly 10, which is the structure that connects to the dental appliance, can be adjustably attached to the abutment section 20 so that the ball section 30 is oriented in parallel or substantially parallel with the orientation of the adjacent anchor L. This parallel orientation permits easier mounting of the dental appliance compared to divergent orientations.

It is to be noted that the angular orientations exemplify some of the many orientations at which the restorative dentist must mount the implant DI due to the patient's specific mandible structure and available bone. As such, the depiction in FIGS. 1A and 1B should be construed as being illustrative. Moreover, a pair of the joint assemblies 10 can be used as anchors instead of in conjunction with the prior art anchor L. It will be understood that an edentulous patient includes one with no teeth or a plurality of missing teeth. Thus, the joint assembly 10 facilitates mounting of various denture appliances/prostheses and the like.

The base member 21 is preferably a cylindrical block or body dimensioned to fit on top of the implant DI. The round shape of the base member 21 conforms to the generally round shape of the gum in the region of the missing tooth, as well as the shape and dimensions of the implant DI. The base member 21 can also be provided in different shapes (e.g., an elongated polygonal body), so long as the shape does not interfere with proper mounting of the dental appliance. Exemplary dimensions of the base member 21 may be, e.g., about 4.3 mm in diameter (equal to that of a regular neck implant DI) and about 3 mm in height, which is also referred to as cuff height. The diameter of the base member 21 may be from about 3 to 5 mm, depending on the diameter of the implant DI being used. Additionally, the cuff height may be about 3 min or more, depending on the height of the soft tissue surrounding the implant DI. It will be understood that the dimensions recited herein are exemplary only, and provided for purposes of enablement, and not for limitation of the invention as claimed.

Figure 3:
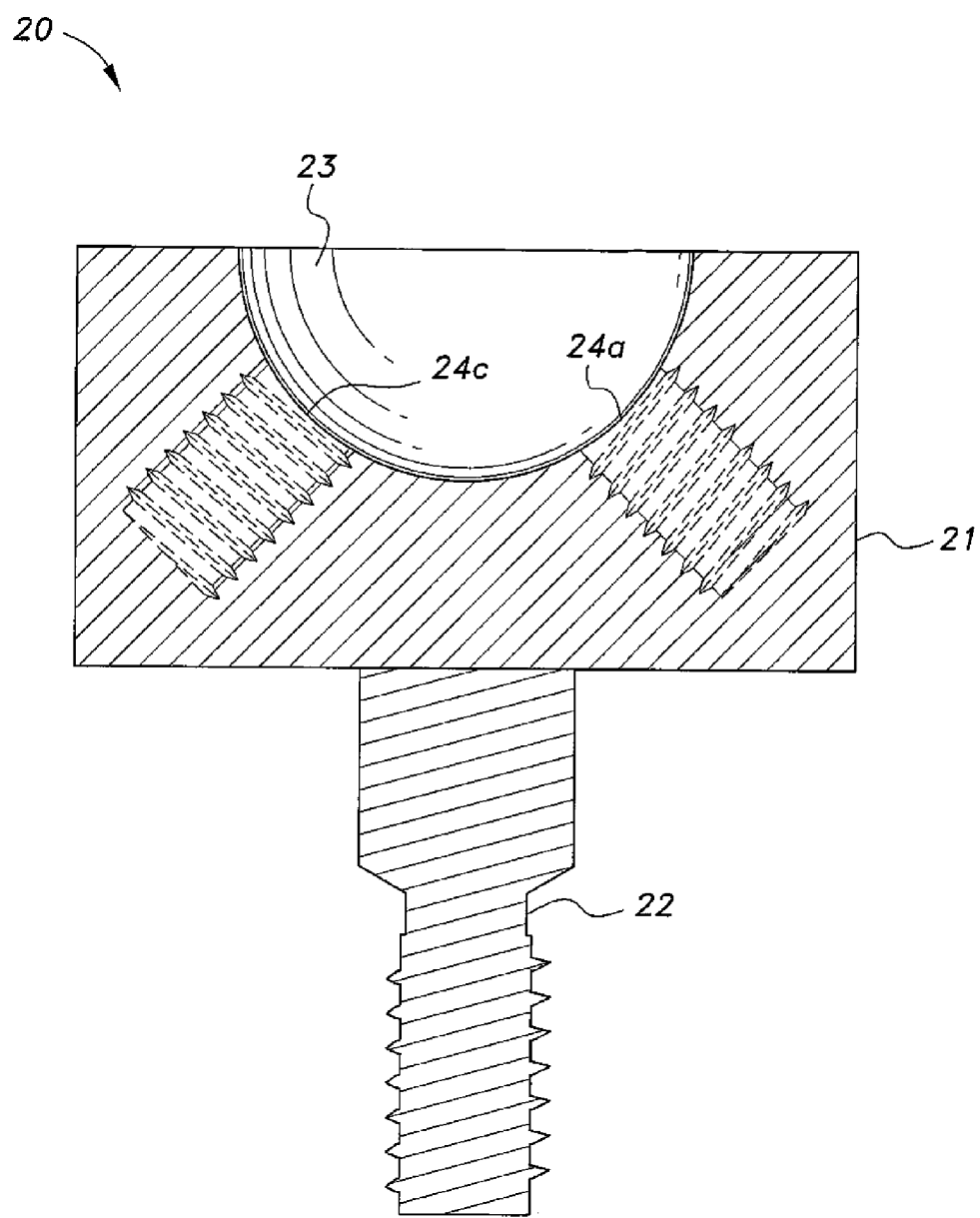
FIG. 3 is a front view in section of an abutment section of the joint assembly for dental implant abutment of FIG. 1.
Figure 4:
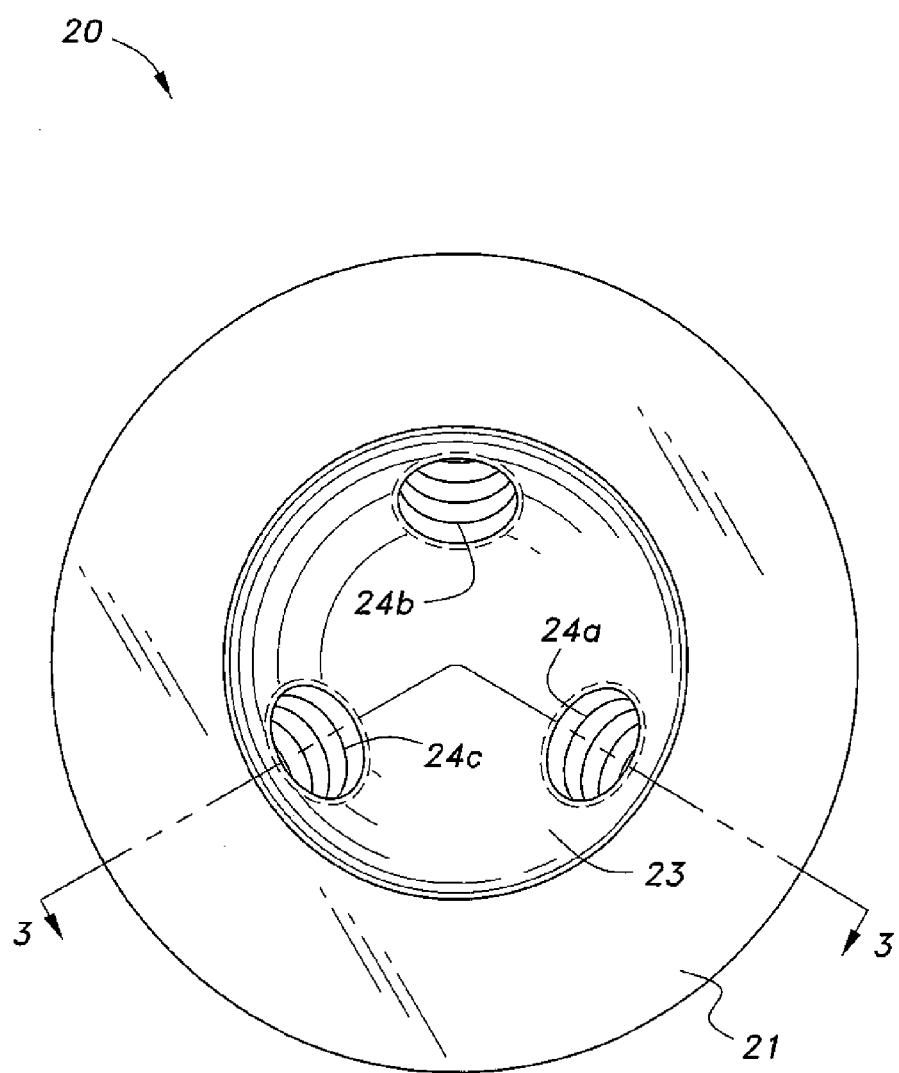
FIG. 4 is a top view of the abutment section of FIG. 3.

As best seen in FIGS. 3 and 4, the top of the base member 21 is substantially planar and provided with a generally hemispherical recess or socket 23 formed therein, which forms a receptacle for installation or mounting of the ball section 30. The socket 23 can also be referred to as a recessed socket 23. To facilitate secure mounting of the ball section 30, the socket 23 includes a plurality of elongate, internally threaded bores 24a, 24b, 24c radiating into the base member 21 or the body of the base member 21 at an angle. The threaded bores 24a, 24b, 24c are preferably distributed equidistantly around the socket 23, and each threaded bore 24a, 24b, 24c extends into the base member 21 at an angle of about 33° with respect to the planar top surface of the base member 21. The threaded bores 24a, 24b, 24c provide the user with selective mounting points from which the ball section 30 can extend to assist the user in properly aligning the joint assembly 10 for effective subsequent mounting of the desired dental appliance. It is to be understood, however, that the number of threaded bores, their relative positions, and their respective angular orientations can be varied as required by the circumstances of the dental surgical procedure.

The dimensions of each threaded bore 24a, 24b, 24c may be about 1 mm in diameter and about 1.5 mm in length. Due to these dimensions, the height of the base member 21 is preferably at least 3 mm to accommodate the desired placement of the threaded bores 24a, 24b, 24c. The socket 23 is preferably about 3.4 mm in diameter, which is smaller than the diameter of the base member 21. This difference in diameters ensures that sufficient material of the base member 21 surrounds the socket 23 to securely support the ball section 30 to be mounted thereon.

Figure 5:
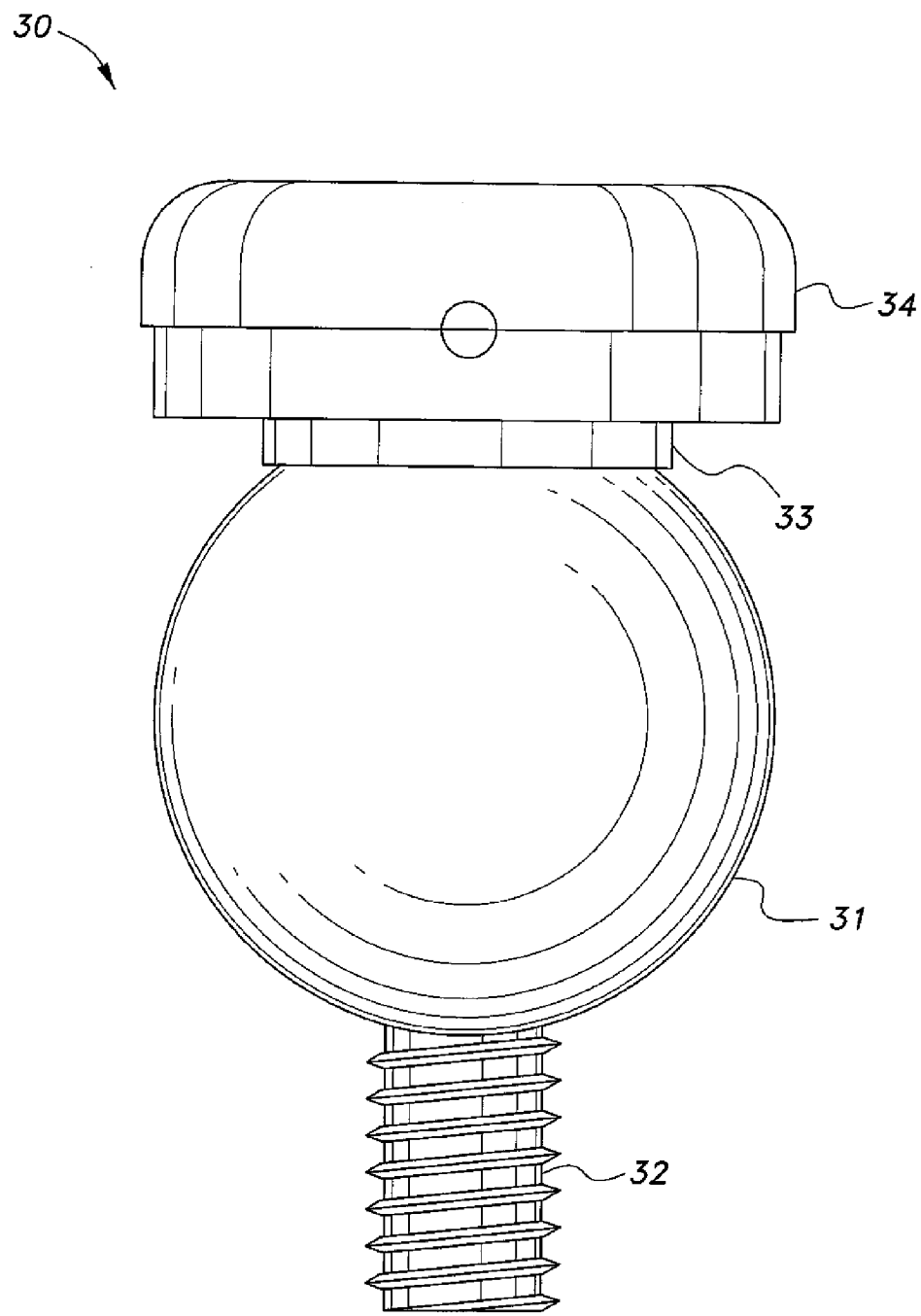
FIG. 5 is a front view of the ball section of the joint assembly for dental implant abutment of FIG. 1.

As best seen in FIGS. 1B and 5, the ball section 30 includes a substantially spherical head 31 configured to be seated inside the socket 23. An elongate, externally threaded post or screw 32 extends from the surface of the spherical head 31. The threads of the externally threaded post 32 have the same number of threads per inch and pitch as the internally threaded bores 24a, 24b, 24c, so that the post 32 may be selectively threaded into a user-selected one of the threaded bores 24a, 24b, 24c to secure the ball section 30 to the abutment section 20 at the desired angle. The ball joint 31 may be about 3.2 mm in diameter, which is slightly less than the diameter of the socket 23, in order to facilitate suitable seating within the socket 23 with minimal tolerance. The threaded post 32 is dimensioned to fit inside any one of the threaded bores 24a, 24b, 24c.

The spherical head 31 also includes an adapter or retention head 33 extending from a diametrically opposite side of the spherical head 31 from the threaded post 32. A mounting cap 34 is retained on the retention head 33. A suitable mounting cap 34 can be provided by the Locator® attachment system described in U.S. Pat. No. 6,030,219, issued to Zuest et al. Feb. 29, 2000, which is hereby incorporated by reference in its entirety. Other suitable mounting caps can be used in the joint assembly 10 with suitable modifications to the retention head 33 to accommodate the specific mounting cap. The mounting cap 34 may be, e.g., about 3.86 mm in width and about 1.78 mm in height.

In use, the abutment section 20 is mounted to the previously installed dental implant DI by torquing the threaded post 22 into the implant DI. Depending on the geometry of the patient's mandible and the optimal installed position and orientation of the implant DI, the restorative dentist selects one of the threaded bores 24a, 24b, 24c to mount the ball section 30 for proper parallel alignment with the other attachment on the other implant for the prosthodontic appliance to be used by the patient. The ball section 30 is mounted to the selected threaded bore 24a, 24b, or 24c by torquing the threaded post 32 into the selected threaded bore 24a, 24b, or 24c.

It is contemplated that the spacing and orientation of the threaded bores 24a, 24b, 24c can accommodate most implant angulations encountered by the restorative dentist. However, irregularities can also be accommodated by forming or drilling threaded bores at the required angle.

It is noted that the joint assembly 10 for dental implant abutment encompasses a variety of alternatives. For example, the joint assembly 10 can be constructed from titanium, titanium alloy, or from any other biocompatible materials safe for intra-oral use.

It is to be understood that the present invention is not limited to the embodiments described above, but encompasses any and all embodiments within the scope of the following claims.

We claim:

1. A joint assembly for dental implant abutment, consisting of:
   an abutment section adapted for attachment to a dental implant, the abutment section consisting of a base defining an upper planar surface having a recessed socket defined therein and a plurality of radially spaced internally threaded bores extending from the recessed socket into the base at an angle with respect to the planar surface and an elongate, externally threaded abutment section post extending from a lower surface of the base, the abutment section post being adapted for engaging a threaded bore in the dental implant to attach the abutment section to the dental implant; and
   a ball section selectively attached to the abutment section, the ball section consisting of:
      a substantially spherical head dimensioned and configured for seating in the recessed socket;
      an elongate externally threaded post extending solely from a single surface of the spherical head, the threaded post selectively engaging one of the plurality of threaded bores in the abutment section to attach the ball section to the abutment section;
      a retention head attached to the spherical head opposite the ball section post; and a mounting cap selectively attached to the retention head, the mounting cap being adapted for attachment of a dental appliance thereto;

wherein selective attachment of the ball section to the abutment section adjustably orients the ball section for proper alignment of the dental appliance in a patient's mouth.

2. The joint assembly according to claim 1, wherein said plurality of threaded bores comprises three threaded bores equidistantly spaced from each other in the recessed socket.

3. The joint assembly according to claim 1, wherein the recessed socket comprises a hemispherical recess.

4. A joint assembly for dental implant abutment, comprising:

an abutment section adapted for attachment to a dental implant, the abutment section having a base defining an upper planar surface having a recessed socket defined therein and a plurality of radially spaced internally threaded bores extending from the recessed socket into the base at an angle with respect to the planar surface and an elongate, externally threaded abutment section post extending from a lower surface of the base, the abutment section post being adapted for engaging a threaded bore in the dental implant to attach the abutment section to the dental implant; and a ball section selectively attached to the abutment section, the ball section having:
- a substantially spherical head dimensioned and configured for seating in the recessed socket;
- an elongate externally threaded post extending solely from a single surface of the spherical head, the threaded post selectively engaging one of the plurality of threaded bores in the abutment section to attach the ball section to the abutment section;
- a retention head attached to the spherical head opposite the ball section post; and
- a mounting cap selectively attached to the retention head, the mounting cap being adapted for attachment of a dental appliance thereto;

wherein selective attachment of the ball section to the abutment section adjustably orients the ball section for proper alignment of the dental appliance in a patient's mouth.

* * * * *